(12) United States Patent
Babu et al.

(10) Patent No.: US 7,078,524 B2
(45) Date of Patent: Jul. 18, 2006

(54) PROCESS FOR THE SYNTHESIS OF GANCICLOVIR

(75) Inventors: Jayachandra Suresh Babu, Haryana (IN); Purna Chandra Ray, Delhi (IN); Yatendra Kumar, Haryana (IN); Chandra Has Khanduri, Haryana (IN)

(73) Assignee: Ranbaxy Laboratories Limited, Haryana, IN (US)

( * ) Notice: Subject to any disclaimer, the term of this patent is extended or adjusted under 35 U.S.C. 154(b) by 226 days.

(21) Appl. No.: 10/302,798

(22) Filed: Nov. 22, 2002

(65) Prior Publication Data

US 2004/0102628 A1 May 27, 2004

(51) Int. Cl.
*C07D 473/18* (2006.01)
*C07B 63/00* (2006.01)

(52) U.S. Cl. .................................. 544/276
(58) Field of Classification Search .......... 544/276
See application file for complete search history.

(56) References Cited

U.S. PATENT DOCUMENTS

| | | | | |
|---|---|---|---|---|
| 4,199,574 A | | 4/1980 | Schaeffer | 424/200 |
| 4,294,831 A | | 10/1981 | Schaeffer | 424/253 |
| 4,355,032 A | | 10/1982 | Verheyden et al. | 424/253 |
| 4,355,034 A | | 10/1982 | Shen et al. | 424/263 |
| 4,816,447 A | | 3/1989 | Ashton et al. | 514/81 |
| 5,565,565 A | * | 10/1996 | Lodewijk et al. | 544/276 |
| 5,583,225 A | * | 12/1996 | Chu et al. | 544/276 |
| 5,756,737 A | | 5/1998 | Turchetta et al. | 544/276 |
| 5,792,868 A | * | 8/1998 | Izawa et al. | 544/276 |
| 5,821,367 A | * | 10/1998 | Kumar et al. | 544/276 |
| 6,043,364 A | | 3/2000 | Kumar et al. | 544/276 |
| 2005/0176956 A1 | * | 8/2005 | Babu et al. | 544/276 |

FOREIGN PATENT DOCUMENTS

| | | |
|---|---|---|
| BE | 833006 | 3/1976 |
| EP | 532 878 | 8/1992 |
| EP | 806 425 | 11/1997 |
| EP | 976 751 | 2/2000 |
| JP | 59-80685 | 5/1984 |
| JP | 63-107982 | 5/1988 |
| PL | 157825 B1 | 8/1988 |

OTHER PUBLICATIONS

Matsumoto, et al., "A Convenient Synthesis of 9–(2–Hydroxyethoxymethyl)guanine (Acyclovir) and Related Compounds". Chem. Pharm. Bull., 36 (3), pp. 1153–1157 (1988).

J.C. Martin, et al., "9–[(1,3–Dihydroxy–2–propowy)methyl] guanine: A New Potent and Selective Antiherpes Agent". J. Med. Chem., 26, pp. 759–761 (1983).

Boryski, et al., "A Facile Synthesis of 9–(1, 3–Dihydroxy–2–propoxymethyl) guanine (Ganciclovir) from Guanosine". Synthesis. 1999, No. 4, pp. 625–628.

Field, et al. "9–{[2–Hydroxy–1–(hydromethyl)ethoxy]methyl} guanine: A selective inhibitor of herpes group virus replication". Proc. Natl. Acad. Sci. Jul. 1983, vol. 80, pp. 4139–4143.

* cited by examiner

*Primary Examiner*—Mark L. Berch
(74) *Attorney, Agent, or Firm*—Jayadeep R. Desmukh, Esq.; George E. Heibel, Esq.

(57) ABSTRACT

The present invention relates to an industrial useful process for the synthesis of antiviral compound, ganciclovir which comprises dissolving a mixture containing N-7 and N-9 isomers of structural formulae, II and III, respectively:

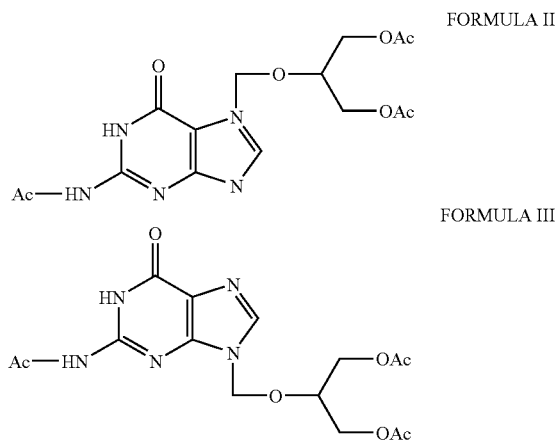

in a solvent or a mixture of solvents; separating the N-7 and N-9 isomers; and hydrolizing the N-9 isomer to obtain ganciclovir.

12 Claims, No Drawings

PROCESS FOR THE SYNTHESIS OF GANCICLOVIR

FIELD OF THE INVENTION

The present invention relates to an industrial useful process for the synthesis of antiviral compound, ganciclovir.

BACKGROUND OF THE INVENTION

Ganciclovir is chemically, 9-(1,3-dihydroxy-2-propoxymethyl) guanine and has the structural formula I:

FORMULA I

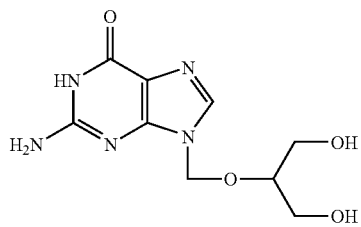

It is one of the most important acyclic nucleosides having significant antiviral properties, especially effective against members of the herpes family and a few other DNA viruses.

The simplest synthetic approach to the N-9 substituted guanine compounds involves the direct alkylation of appropriately substituted 2-aminopurines e.g. guanine derivatives. However, the major drawback in this process is that it always results in a mixture of N-9 and N-7 alkylation products. Since alkylation of guanine derivatives like diacetyl/monoacetyl guanine is a thermodynamically controlled reaction, N-7 isomer is always formed. However, the N-9 isomer being thermodynamically more stable is produced as the major product. The unwanted N-7 isomer is difficult to separate from the desired N-9 isomer and is generally purified by costly and tedious processes requiring chromatographic separation and are highly undesirable on a commercial scale.

Some of the prior art processes for the manufacture of aciclovir/ganciclovir are disclosed in BE 833006; U.S. Pat. Nos. 4,199,574 and 4,355,032; Chem Pharm Bull, 36 (3) 1153–1157 and JP 63-107982 and 59-80685, and EP 532878. One such U.S. Pat. No. 5,821,367 describes a regiospecific process which comprises reacting protected guanine derivative with an alkylating agent selected from 2-oxa-1,4-butanediol diacetate, 1-4-diacetoxy-3-acetoxymethyl-2-oxa-butane, and 1,4-dibenzyloxy-3-acetoxymethyl-2-oxabutane in the absence of solvent or any acid catalyst to obtain the penultimate intermediates which are then converted to acylic nucleosides (acyclovir and ganciclovir). U.S. Pat. No. 6,043,364 teaches a process for the conversion of N-7 isomer to N-9 isomer by heating a suspension of the N-7 isomer in an alkylating agent.

However, the separation of N-9 isomer from the form N-7 isomer in said patent has been achieved by column chromatography only. Therefore, the process does not offer any additional benefits from commercial point of view.

Accordingly, none of the processes heretofore described are completely satisfactory.

SUMMARY OF THE INVENTION

It is an object of the present invention to provide a simplified, commercially feasible process which gives the desired product in good yield, utilizing easily available commercial raw materials. The crystallization procedure of the present invention is very simple and produces the N-9 isomer having more than 95% purity which can directly be used for the preparation of ganciclovir. The present process is cost effective and obviates the need for chromatographic separation.

According to another aspect of the present invention, the N-7 isomer so separated is recycled in the next batch of alkylation. It has been observed that the recycling of the N-7 isomer during alkylation enhances the formation of N-9 isomer and decreases the formation of N-7 isomer in the subsequent batches. This recycling of the side product improves the overall yield of the N-9 isomer and consequently the desired product i.e. ganciclovir.

Thus, the present invention provides a process which does not require discarding the unwanted N-7 isomer or an additional step of conversion of the N-7 isomer to N-9 isomer thereby providing an in-situ conversion to the desired N-9 isomer.

DETAILED DESCRIPTION OF THE INVENTION

Accordingly, the present invention provides a process for the separation of N-7 and N-9 isomers of structural formulae II and III, respectively,

FORMULA II

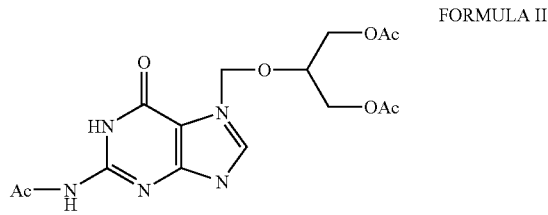

FORMULA III

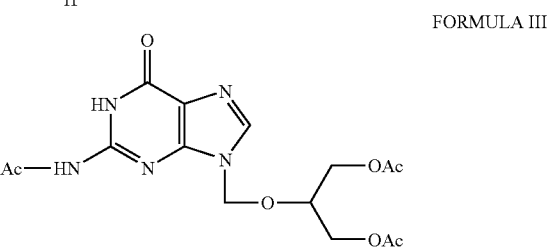

which comprises dissolving a mixture comprising the N-7 and N-9 isomers in an organic solvent, or a mixture of organic solvents, and isolating the N-7 and N-9 isomers from a solution thereof.

The choice of solvent has been found to be important for the separation of N-7 and N-9 isomers. We have found that the two isomers of structural formulae II and III have different solubilities, one of them being consistently more soluble than the other. The levels of solubility vary according to the solvent, and so a solvent system will desirably be chosen which allows a practical recovery of the two isomers that is present prior to the separation.

The solvent system from which the isomers may be separated will desirably be selected from alcoholic solvents, which include lower alkanols, water-immiscible solvents, or a mixture thereof. The N-7 isomer of structural formula II will preferably be separated from the solvent system which has at least one lower alkanol. The lower alkanols include primary, secondary and tertiary alcohols having from one to six carbon atoms, for example, methanol, ethanol, n-propyl alcohol, isopropyl alcohol, isobutanol, n-butanol, tertiary butanol, or mixtures thereof. Most preferred being methanol, ethanol, or isopropyl alcohol.

The N-9 isomer of structural formula III will preferably be separated from a solvent system which in addition to alcoholic solvents may contain water-immiscible solvents which include aromatic hydrocarbons such as benzene, toluene, or xylene, and chlorinated hydrocarbons such as chloroform, dichloromethane, or 1,2-dichloroethane.

In accordance with the present invention, after the N-7 isomer is separated, the concentration of the filtrate containing the N-9 isomer is adjusted by evaporation of the solvent or by dilution.

The separation may comprise the last stage or stages of a reaction in which the mixture of N-7 and N-9 isomers is formed. The reaction in which ganciclovir of the structural formula I, is formed will preferably be an alkylation reaction carried out in the manner described in U.S. Pat. No. 4,355,032 which is incorporated herein by reference.

Methods known in the art may be used with the process of this invention to enhance any aspect of this invention. For example, the solution containing the mixture of N-7 and N-9 isomers may be heated for dissolution, or it may be cooled to separate out the product or the slurry may further be cooled prior to filtration.

The N-7 isomer of structural formula II so separated is used in the next batch of alkylation. Accordingly, a mixture of diacetyl guanine of Formula IV

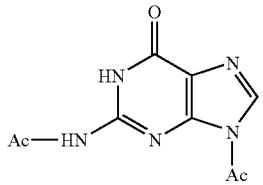

FORMULA IV and 2-acetoxymethoxy-1,3-diacetoxypropane of Formula V:

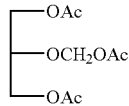

FORMULA V is reacted in the presence of an acid catalyst and $N^2$-acetyl-7(1,3-diacetoxy-2-propoxymethyl) guanine (the N-7 isomer), in an organic solvent. After the reaction is completed, the solvent is removed under vacuum to yield a dark oil from which N-7 and N-9 isomers are separated in accordance with the process of the present invention and N-7 isomer is again recycled.

The N-9 isomer so obtained after separation is hydrolyzed to yield ganciclovir by the methods known in the literature (J. E. Martin et. al., J. Med. Chem., 1983, 26, 759–61).

The present invention is illustrated by the following examples, which are not intended to limit the effective scope of this invention in any way.

EXAMPLE—1

A mixture of diacetyl guanine (25 g, 0.106 mole), 2-acetoxymethoxy-1,3-diacetoxy propane (40.0 g, 0.161 mole), p-toluene sulfonic acid monohydrate (0.5 g) in N,N-dimethylformamide (75 ml) is heated at 95° C. to 100° C. under continuous stirring for 42 hours. After completion of the reaction, the solvents are removed under vacuum yielding a dark brown syrup.

The syrup is dissolved by heating in methanol (60 ml). The resulting solution is stirred at room temperature, cooled to 0° C., stirred for 30 min. at 0–5° C. The crystallized material is filtered and washed with methanol (2×40 ml) to yield $N^2$-acetyl-7-( 1,3-diacetoxy-2-propoxymethyl) guanine (7.67 g).

The solvent from the filtrate is removed completely by distillation under reduced pressure to give an oily syrup. The oily syrup is dissolved in isopropyl alcohol and filtered through celite. The solvent is distilled off completely under vacuum. The residue is heated with a mixture of methanol (20 ml) and toluene (150 ml) at 60° C., stirred at room temperature and then at 0–5° C. for 30 minutes. The product is filtered and washed with a mixture of methanol and toluene (1:4) to yield $N^2$-acetyl-9-(1,3-diacetoxy-2-propoxymethyl) guanine (11.0 g).

EXAMPLE—2

A mixture of diacetyl guanine (100 g, 0.425 mole), 2-acetoxymethoxy-1,3-diacetoxy propane (150 ml, 0.605 mole), p-toluene sulfonic acid monohydrate (2.0 g), $N^2$-acetyl-7-(1,3-diacetoxy-2-propoxymethyl) guanine (70 g) in N,N-dimethylformamide (400 ml) is heated at 90° C. to 100° C. under continuous stirring for 63 hours. After completion of the reaction, the solvents are removed under vacuum from the reaction mixture, yielding a dark brown syrup.

The syrup is dissolved by heating in methanol (400 ml). The solution is cooled to 0° C., stirred for 1 hour at 0 to 5° C. The crystalline product is filtered and washed with methanol (2×100 ml) to yield $N^2$-acetyl-7-(1,3-diacetoxy-2-propoxymethyl) guanine (69.0 g).

Solvent is removed completely from the filtrate and methanol (100 ml) and toluene (800 ml) are added to the residue and the mixture is heated to 60° C. and then cooled to 5° C. and stirred for 30 minutes. The crystalline product is filtered, washed with a mixture of methanol and toluene (1:4), dried at 60–65° C. to afford $N^2$-acetyl-9-(1,3-diacetoxy-2-propoxymethyl) guanine (107.0 g).

EXAMPLE—3

A mixture of diacetyl guanine (100 g, 0.425 mole), 2-acetoxymethoxy-1,3-diacetoxy propane (180 g, 0.725 mole), p-toluene sulfonic acid monohydrate (5.0 g), $N^2$-acetyl-7-(1,3-diacetoxy-2-propoxymethyl) guanine (78 g) in N,N-dimethylformamide (350 ml) is heated at 95° C. to 100° C. under continuous stirring for 40 hours. After completion of the reaction, the solvents are removed under vacuum from the reaction mixture, yielding a dark brown syrup.

The syrup is dissolved by heating in methanol (400 ml). The solution is cooled to 0° C., stirred for 1 hour at 0 to 5° C. The crystalline product is filtered and washed with methanol (50 ml) to yield $N^2$-acetyl-7-(1,3-diacetoxy-2-propoxymethyl) guanine (54.1 g).

Solvent is removed completely from the filtrate and methanol (100 ml) and toluene (800 ml) were added to the residue and the mixture is heated to 60° C. and then cooled to 5° C. and stirred for 30 minutes. The crystalline product is filtered, washed with a mixture of methanol and toluene (1:4), dried at 60–65° C. to afford $N^2$-acetyl-9-(1,3-diacetoxy-2-propoxymethyl) guanine (114.0 g).

While the present invention has been described in terms of its specific embodiments, certain modifications and equivalents will be apparent to those skilled in the art and are intended to be included within the scope of the present invention.

We claim:

1. A process for the separation of N-7 and N-9 isomers of structural formulae II and III, respectively:

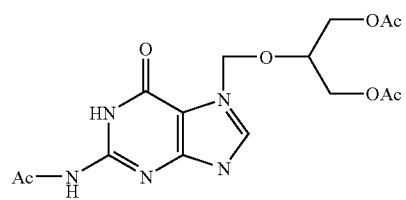

FORMULA II

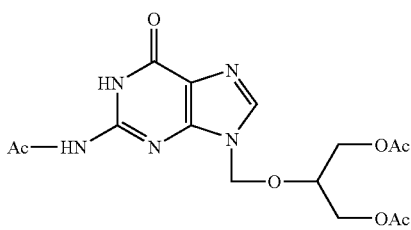

FORMULA III wherein Ac represents acetyl, the process comprising disolving a mixture containing the N-7 and N-9 isomers in one or more alcoholic solvents to get a solution; separating the N-7 isomer from the solution thereof by filtration; removing the solvent from filtrate to obtain a residue; adding another solvent or a mixture of solvents, wherein the solvent comprises one or more of alcoholic solvents and water immiscible solvents; and isolating the N-9 isomer.

2. The process of claim 1, wherein the alcoholic solvents include primary, secondary and tertiary alcohols having from one to six carbon atoms.

3. The process of claim 2 wherein the alcoholic solvent is selected from the group consisting of methanol, ethanol, n-propyl alcohol, isopropyl alcohol, n-butanol, isobutanol, tertiary butanol, and mixtures thereof.

4. The process of claim 3 wherein the solvent is methanol, ethanol or isopropyl alcohol.

5. The process of claim 1, wherein the water immiscible solvent includes aromatic or chlorinated hydrocarbons.

6. The process of claim 5 wherein the aromatic hydrocarbon is selected from the group consisting of toluene, benzene, xylene and mixtures thereof.

7. The process of claim 6 wherein the chlorinated hydrocarbon is selected from the group consisting of dichloromethane, chloroform, 1,2-dichloroethane, and mixtures thereof.

8. A process for the hydrolysis of N-9 isomer of formula III:

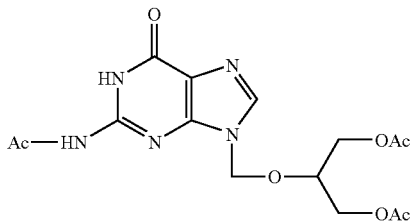

FORMULA III obtained by the process of claim 1 to give ganciclovir of Formula I:

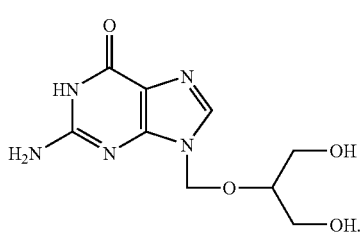

FORMULA I

9. The process of claim 1, further comprising cooling the solution before separating the N-7 isomer.

10. The process of claim 9, wherein the solution is cooled at a temperature from 0° C. to 5° C.

11. The process of claim 1, wherein the solvent is removed by distillation under reduced pressure.

12. The process of claim 1, wherein the N-9 isomer is isolated by filtration.

* * * * *